United States Patent
Charette (10) Patent No.: US 7,997,148 B2
(45) Date of Patent: Aug. 16, 2011

(54) SYSTEMS AND METHODS FOR INTERCEPTING SUBMARINE GROUNDWATER FOR DESALINATION

(75) Inventor: Matthew Charette, East Falmouth, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 50 days.

(21) Appl. No.: 12/403,287

(22) Filed: Mar. 12, 2009

(65) Prior Publication Data

US 2009/0241685 A1     Oct. 1, 2009

Related U.S. Application Data

(60) Provisional application No. 61/069,085, filed on Mar. 12, 2008.

(51) Int. Cl.
*G01F 1/708* (2006.01)
*G01F 1/00* (2006.01)
(52) U.S. Cl. .................... 73/861.05; 73/861
(58) Field of Classification Search ............ None
See application file for complete search history.

(56) References Cited

U.S. PATENT DOCUMENTS

| | | | |
|---|---|---|---|
| 5,497,663 | A | 3/1996 | Reay et al. |
| 5,594,179 | A | 1/1997 | Marsh |
| 6,276,217 | B1 | 8/2001 | Hirano et al. |
| 6,622,093 | B1 | 9/2003 | Fujinawa et al. |
| 6,874,371 | B1 | 4/2005 | Smith et al. |
| 6,938,495 | B2 | 9/2005 | Hirano et al. |
| 7,107,859 | B2 | 9/2006 | Smith et al. |
| 7,637,168 | B2 * | 12/2009 | Charette .............. 73/861.05 |

FOREIGN PATENT DOCUMENTS

| | | |
|---|---|---|
| EP | 0 448 089 A2 | 9/1991 |
| JP | 62025239 | 2/1987 |
| WO | WO-2004/081544 A1 | 9/2004 |

OTHER PUBLICATIONS

Importance of Submarine Groundwater Discharge and Seawater Cycling to material flux across sediment/water interfaces in marine envoronements. By George M. Simmons, Jr. vol. 84, pp. 173-184, Pub. Jul. 30, 1992.*
U/Th Series Radionuclides as Coatal Groundwater Tracers, by P. W. Swarzenski, Rev. 2007, 107, pp. 663-674.*
Submarine Groundwater Discharge: An Introduciton, USGS—PAcific Coastal & Marine Science Center, Mod. Jan. 22, 2010.*

(Continued)

*Primary Examiner* — Harshad Patel
(74) *Attorney, Agent, or Firm* — Ropes & Gray LLP (57) ABSTRACT

The systems and methods described herein allow for intercepting submarine groundwater discharge to be used as a supply source for desalination processes. In one practice a dye-dilution seepage meter is employed as a device for locating water sources. These meters can be placed in estuaries and other locations that may be candidate locations to test for flows of groundwater. In areas of suspected SGD, the meters can be deployed to quantify the potential yield and quality (e.g. salt content) of the resource. Regarding the water quality, it is important to note that even brackish water sources can greatly reduce the energy needed to achieve potable water by desalination.

20 Claims, 7 Drawing Sheets

OTHER PUBLICATIONS

Bokuniewicz et al., "Direct measurements of submarine groundwater discharge (SGD) over a fractured rock aquifer in Flamengo Bay Brazil," Estuarine Coastal and Shelf Science, 76(3):466-472 (2007).

Sholkovitz et al., "An automated dye-dilution based seepage meter for the time-series measurement of submarine groundwater discharge," Limnology and Oceanography: Methods, 1:16-28 (2003).

Tryon et al., "A new benthic aqueous flux meter for very low to moderate discharge rates," Deep-Sea Research Part I, 48:2121-2146 (2001).

International Search Report for PCT/US2008/010617 dated May 8, 2009.

International Search Report and Written Opinion for PCT/US2009/037010 mailed Sep. 15, 2010.

* cited by examiner

SYSTEMS AND METHODS FOR INTERCEPTING SUBMARINE GROUNDWATER FOR DESALINATION

CROSS-REFERENCE TO RELATED APPLICATIONS

This application claims the benefit of U.S. Provisional Application Ser. No. 61/069,085, filed on Mar. 12, 2008. The teachings of the foregoing application are hereby incorporated by reference herein in their entirety.

BACKGROUND OF THE INVENTION

The quality and availability of freshwater resources are becoming increasingly stressed as coastal human populations rise throughout the globe. In existing and emerging coastal cities where surface water pollution increases and supply declines (often triggered by changing climate), governments may turn to groundwater as an alternative source; those that have done so already may not be utilizing this resource using best management practices. In arid climates, countries are already relying on desalination of coastal seawater for the majority of their freshwater needs. For example, the acute lack of natural water resources and the wealth of Kuwait have created a unique water sector where about 90% of the potable water production comes from seawater desalination. Though this unusual situation has been maintained for decades, and probably will continue into the foreseeable future, it has resulted in serious drawbacks. At a per capita demand of 493 L/day and a $3/cubic meter production cost, the ever-increasing economic burden of satisfying the water demand is bound to slowdown the pace of development.

Thus, although desalination is an effective way to generate a fresh water supply for a coastal community, the process can be expensive and this expense can interfere with the ready availability of potable water to the local population.

Thus there exists a need to develop desalination processes that are more cost effective.

In many instances where desalination is used, the processes are not as efficient as possible and in particular fail to harvest coastal groundwater as the supply source. This can result in coastal groundwater being underutilized and lost to the ocean via submarine groundwater discharge (SGD), or trapped in offshore aquifers. Once it exits the aquifer, the freshwater component of SGD is lost to the sea. Recovery of this resource for desalination (or direct use) purposes has been under consideration for a number of years and has been tested through a number of feasibility studies. The Municipal Water District of Orange County (MWDOC) has installed a slant well into the beach-face near Dana Pt., Calif. (http://www.mwdoc.com/). There, brackish to saline groundwater will be extracted and desalinated at a soon to be constructed test facility. A French company has successfully mined offshore SGD (mainly as freshwater springs) in a number of countries around the world (http://www.nympheawater.com/).

SUMMARY OF THE INVENTION

The systems and methods described herein allow for intercepting submarine groundwater discharge to be used as a supply source for desalination processes. In one practice a dye-dilution seepage meter is employed as a device for locating water sources. These meters can be placed in estuaries and other locations that may be candidate locations to test for flows of groundwater. In areas of suspected SGD, the meters can be deployed to quantify the potential yield and quality (e.g. salt content) of the resource. Regarding the water quality, it is important to note that even brackish water sources can greatly reduce the energy needed to achieve potable water by desalination.

Once resources are tapped, the meters can be used as part of a monitoring network designed to ensure that extraction rate does not exceed the natural output of the source. In such an application, the seepage meter would be monitoring for a change in the salt content of the SGD or excessive seawater intrusion into the aquifer (also known as "reverse flow").

Once the devices have identified viable source of groundwater discharge, the desalination plant, will by way of an extended in-flow pipe to the location of the groundwater discharge to capture the groundwater for use by the desalination plant. The devices can then become part of a water source and inflow control system that monitors and controls how the desalination plant pulls in water for processing. It is understood that use of this identified water supply will reduce the energy needed to produce potable water.

To these ends, the systems and methods described herein include, among other things, a groundwater discharge detection system that includes an automated seepage meter, as well as networks, and other arrangements, of automated seepage meters, that detect and quantify groundwater outflow and seawater infiltration. In one embodiment, the meters employ a dye-dilution technique, that provides high resolution time series data for submarine groundwater discharge to the coastal zone. The dye dilution method involves two repeatable steps: (1) the timed injection of a water-soluble dye into a dye mixing chamber mounted in series with a seepage chamber and (2) the subsequent timed measurements of the absorbance of the dyed solution. The rate at which the dyed solution is diluted by the inflow or outflow of water is directly proportional to the flow rate of groundwater moving through the surface area of the seepage housing. In certain example embodiments described herein a fiber optic absorbance meter is placed within a mixing chamber into which groundwater is flowed. Injected into the flowing groundwater is a water soluble dye that will color the flowing groundwater. The fiber optic absorbance meter measures the relative proportion of dye within the mixing chamber and, through a series of timed measurements, measures the rate at which the dye is diluted within the mixing chamber. This, therefore measures the rate at which groundwater passes through the mixing chamber and is representative of the rate of flow of the groundwater.

Accordingly, in one aspect, the invention provides methods for detecting and monitoring submarine groundwater discharge suitable for desalination that comprise providing at least one submersible seepage meter capable of measuring water salinity, disposing the seepage meter at at least one interface between a coastal aquifer and a body of saline water, and measuring, with the seepage meter, a flow of water through the interface, the flow direction of the flow of water, and the salinity of the flow of water. Optionally, the at least one seepage meter is automated. In certain embodiments, the at least one seepage meter comprises a plurality of seepage meters disposed in a network for detecting and monitoring the flow of water through the at least one interface. The at least one interface may be at the bottom of the body of saline water, and the at least one seepage meter may be submerged in and disposed at the bottom of the body of saline water.

In another aspect, the invention provides systems for detecting and monitoring submarine groundwater discharge suitable for desalination that comprise at least one submersible seepage meter capable of measuring water salinity, disposed at at least one interface between a coastal aquifer and a body of saline water, and configured to measure a flow of water through the at least one interface, measure a flow direction of the flow of water through the at least one interface, and measure the salinity of the flow of water through the at least one interface.

In all of the above aspects and embodiments, the at least one seepage meter may be a dye-dilution seepage meter, and includes a mixing chamber with a dye injector for making timed injections of a water soluble dye into the mixing chamber, a pump for distributing the dye equally about the chamber, and an optical absorbance meter in the chamber with a light source and a light receiver for passing a beam of light through the fluid flowing through the chamber and measuring a characteristic representative of absorbance of a wavelength of light, respectively. The dye-dilution seepage meter may also include a processor for processing the measured characteristics to determine a rate of flow for fluid passing through the at least one interface. Optionally, the seepage meter may include a timer for making a series of timed measurements and dye injections for determining a rate of flow of water through the at least one interface and/or a background sensor for measuring a characteristic representative of absorbance of a wavelength of light of fluid in the chamber and absent the injected dye. In certain embodiments, the seepage meter may include a sensor for measuring a direction of fluid flow and/or a chemical sensor for detecting and determining the rate of flow of at least one chemical element flowing through the interface, and wherein measuring the flow direction of the flow of water through the interface comprises measuring the flow direction with the sensor and measuring the salinity of the flow of water through the interface comprises measuring the salinity with the chemical sensor. In all of the above aspects and embodiments, the at least one submersible seepage sensor may include a watertight housing.

BRIEF DESCRIPTION OF THE DRAWINGS

The foregoing and other objects and advantages of the invention will be appreciated more fully from the following further description thereof, with reference to the accompanying drawings wherein.

DETAILED DESCRIPTION

To provide an overall understanding of the systems and methods described herein, certain illustrative embodiments will now be described, including a method and system for intercepting submarine groundwater discharge to be used as a supply source for desalination processes. In particular, a network of strategically-placed seepage meters is described, along with an example of a seepage meter that may be used in the network. However, it will be understood by one of ordinary skill in the art that the systems and methods described herein can be adapted and modified for other suitable applications and that such other additions and modifications will not depart from the scope hereof.

Figure 1:
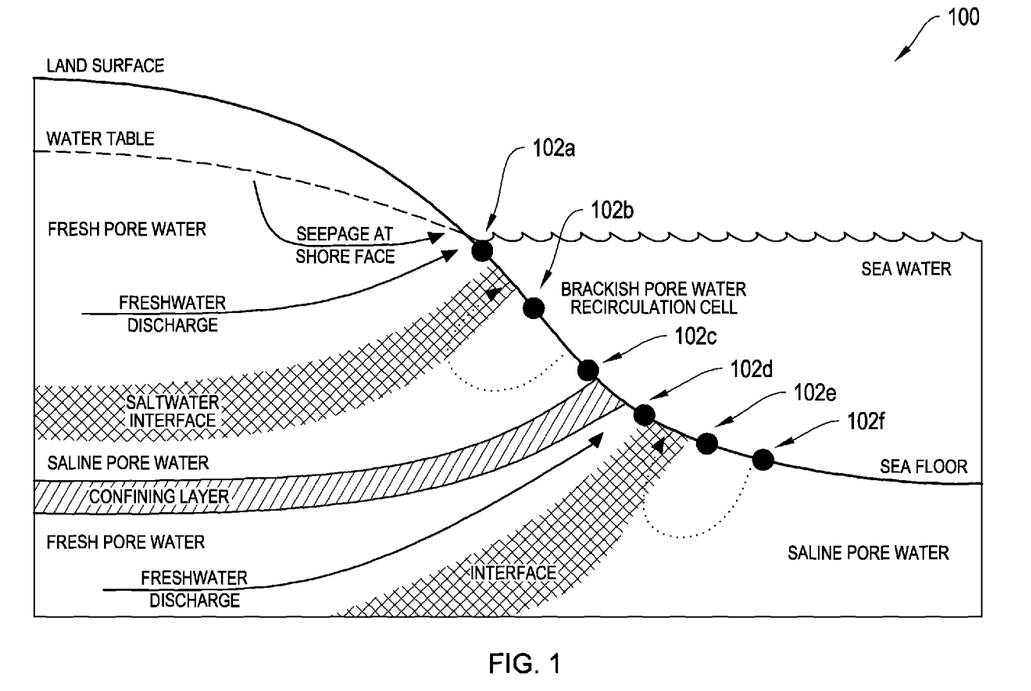
FIG. 1 is a depiction of a network of seepage meters deployed in seawater according to an embodiment of the invention.

FIG. 1 is a depiction from the side of a network of seepage meters 100 deployed to detect and monitor submarine groundwater discharge according to an embodiment of the invention. Submarine groundwater discharge (SGD) is the flow of water from coastal aquifers into the ocean. Most SGD derives from inland precipitation that recharges aquifers, and then flows into the sea. The cross section in FIG. 1 shows the principle features of a coastal groundwater system. Freshwater flowing down gradient from the water table may either discharge from a seepage face at the shore, or flow directly from the saltwater interface into the sea. The hydraulic gradient, which drives freshwater toward the sea along the interface also, drives saltwater back to sea, creating a saltwater circulation cell. If multiple aquifers and confining layers exist, then each aquifer will have a saltwater interface, and deeper aquifers may discharge farther off shore. The network 100 of seepage meters 102a-102f may be placed to detect and monitor SGD at the saltwater interface. The location and placement of individual seepage meters may vary depending on the groundwater discharge characteristics. For example, if multiple aquifers are discharging groundwater, as shown in FIG. 1, the use of the network 100 of multiple seepage meters may be desirable in order to locate the multiple discharge sites as well as to provide adequate monitoring of the groundwater discharge process. If there is only one aquifer discharging groundwater, multiple seepage meters may still be desirable, because the aquifer may discharge groundwater at multiple depths, and may also being discharging groundwater at different locations due to, for example, erosion.

Figure 2:
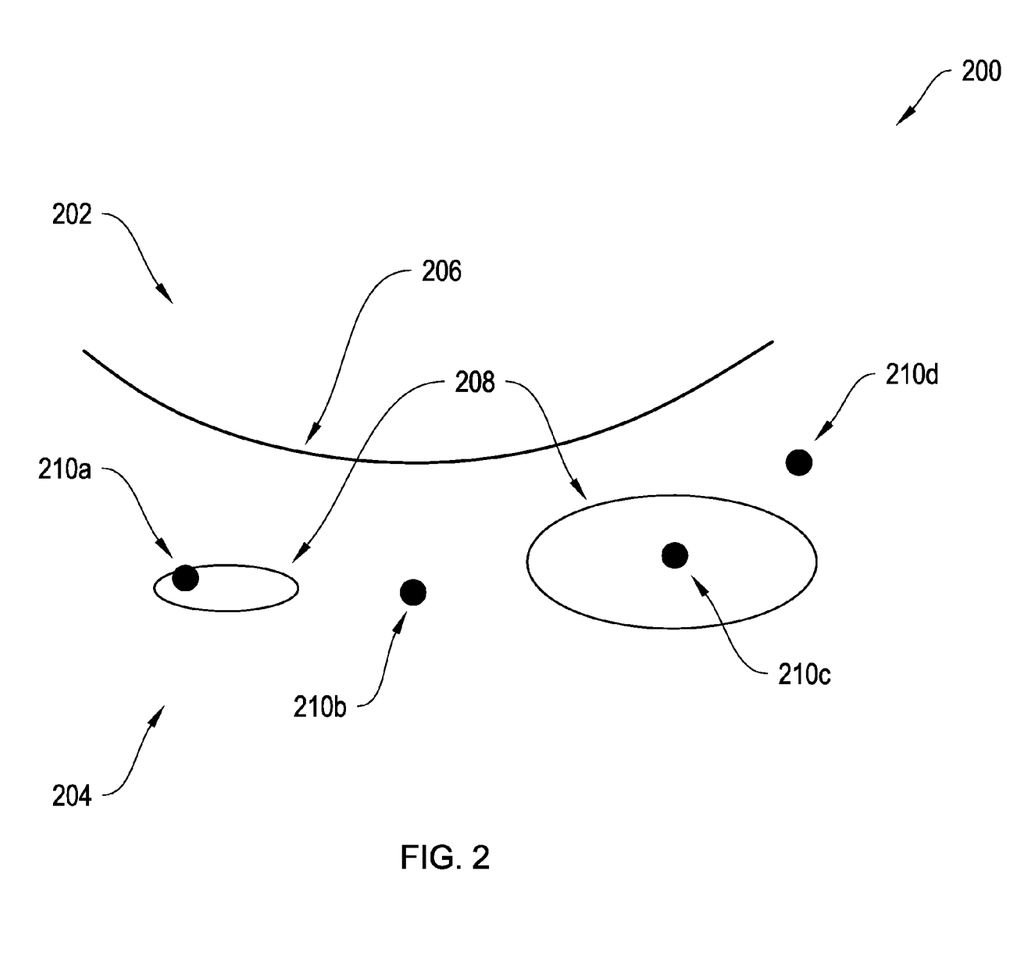
FIG. 2 is a second depiction of a network of seepage meters deployed according to an embodiment of the invention.

FIG. 2 is a depiction from above of a network 200 of seepage meters deployed to detect and monitor SGD according to an embodiment of the invention. Seepage meters 210a-d may be positioned at a coastal region, where 202 is land, 204 is a body of water, and 206 is the coastline delineating the boundary between land 202 and water body 204. One or more coastal aquifers may discharge groundwater at locations 208. The placement of the network 200 of seepage meters 210a-d may assist in the initial detection of SGD. For example, if water of lower salinity than the water in water body 204 is detected by meters 210a and 210c and meters 210b and 210c do not detect water of lower salinity than the water in water body 204, then that may be an indication that SGD is occurring at the locations of meters 210a and 210c. Similarly, if meters 210a and 210c detect flows of water into water body 204, that may be an indication of SGD at the locations of meters 210a and 210c.

Once SGD locations have been detected by seepage meter networks 100 and/or 200, determinations of whether it is feasible to recover the SGD for desalination can be done. The economic feasibility of recovering SGD for desalination may depend on a number of factors, such as, for example, cost of water in that coastal region, distance to the nearest desalination facility, flow rate of the SGD, and the relatively salinity of the SGD compared to the salinity of water body 204. If it is deemed desirable to recover the SGD for desalination, pipes or other methods for recovering the SGD may be put in place, and the seepage meter networks 100 and/or 200 may be left in place to continue monitoring the SGD. Changes detected in SGD salinity or SGD flow by seepage meter networks 100 and/or 200 may assist in controlling the desalination process at the desalination facility. For example, if SGD salinity increases, or SGD flow decreases or reverses, the aquifer may be being tapped faster than it is being replenished. In this case, it may be desirable to lower the throughput of the desalination facility to allow the aquifer to replenish.

In certain embodiments, the seepage meters 102*a-f* and 210*a-d* may employ a dye-dilution technique that provides high resolution time series data for submarine groundwater discharge to the coastal zone. The dye dilution method includes two repeatable steps: (1) the timed injection of a water-soluble dye into a dye mixing chamber mounted in series with a seepage chamber and (2) the subsequent timed measurements of the absorbance of the dyed directly proportional to the flow rate of groundwater moving through the surface area of the seepage housing.

Figure 3A:
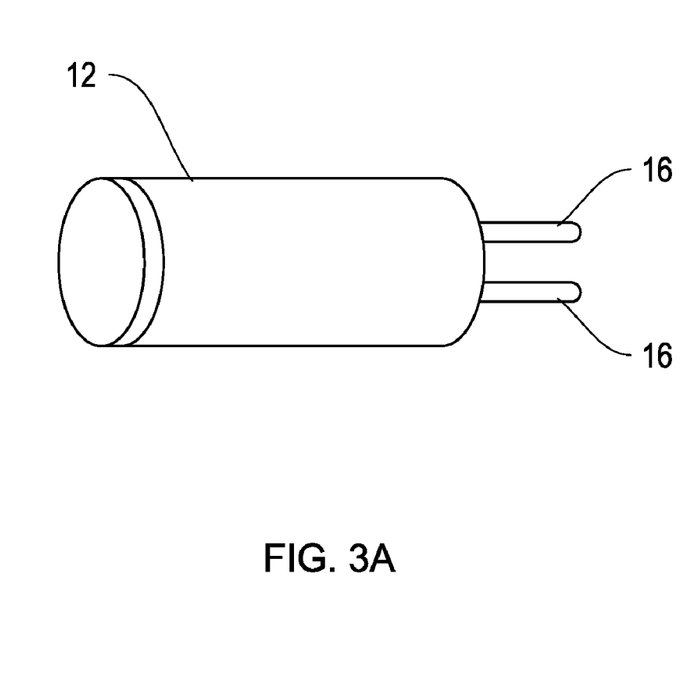
FIGS. 3A and 3B depict a seepage meter according to an embodiment of the invention.
Figure 3B:
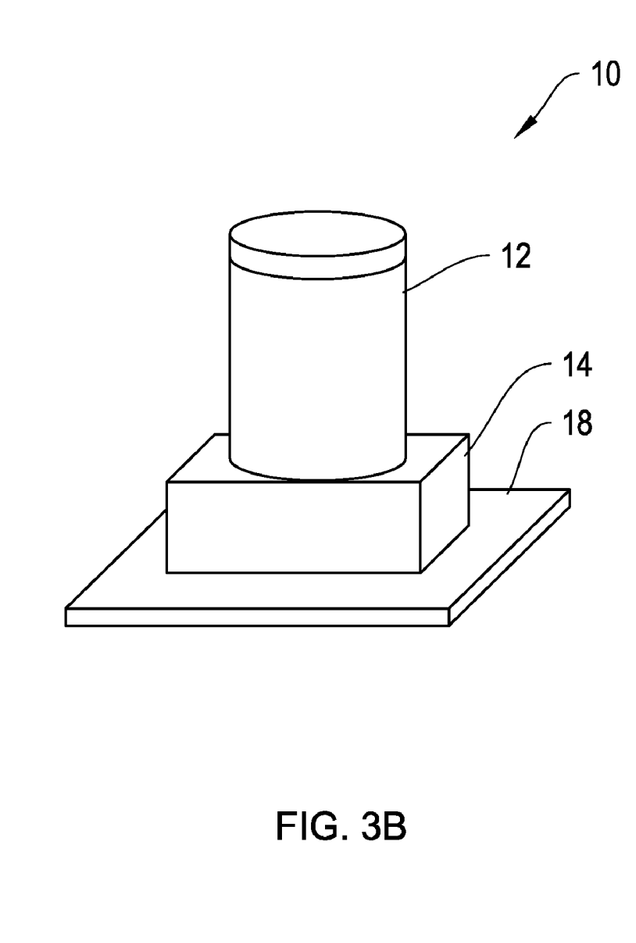

FIGS. 3A and 3B depict a first embodiment of a seepage meter for sampling the candidate locations. In particular FIG. 3A depicts an absorbance meter of the type desired herein and FIG. 3B depicts a seepage meter using the absorbance meter depicted in FIG. 3A. In particular, FIG. 3B depicts a seepage meter 10 that includes an absorbance meter 12 positioned above a mixing chamber 14. The depicted absorbance meter 12 includes two sensor probes 16 that may pass into the mixing chamber 14 to measure characteristics that are representative of the rate of flow of fluid through the chamber 14. In the depicted embodiment, the absorbance meter 12 is depicted as being on top of the mixing chamber 14 thereby having the sensor probes 16 enter into the mixing chamber from the top. However, other embodiments and configurations may be employed and optionally, the fiber optic probes may enter the mixing chamber 14 from the side, to thereby avoid putting the weight of the pressure housing on the two probes and the chamber 14. The mixing chamber 14 is seated on and connected to a base 18 and the base 18 is capable of being deployed on to the ocean floor in such a way as to maintain the device 10 in a relatively stable state. As shown in FIG. 3A the absorbance meter 12 includes, in this embodiment, two stainless steel sensor elements 16 that extend outwardly from the housing of the absorbance meter. Additional optional elements, including battery power supplies, telemetry equipment, thermostats, water samplers, pumps for pumping dyes, groundwater and other fluids, and other sensors may also be contained in the housing of the meter 10. For example, sensors to detect fluid flow direction, fluid salinity, or other fluid characteristics may be contained in the housing of the meter 10. In certain embodiments, one or more seepage meters may be stand alone or networked together to provide information such as the daily rate of flow.

Figure 4:
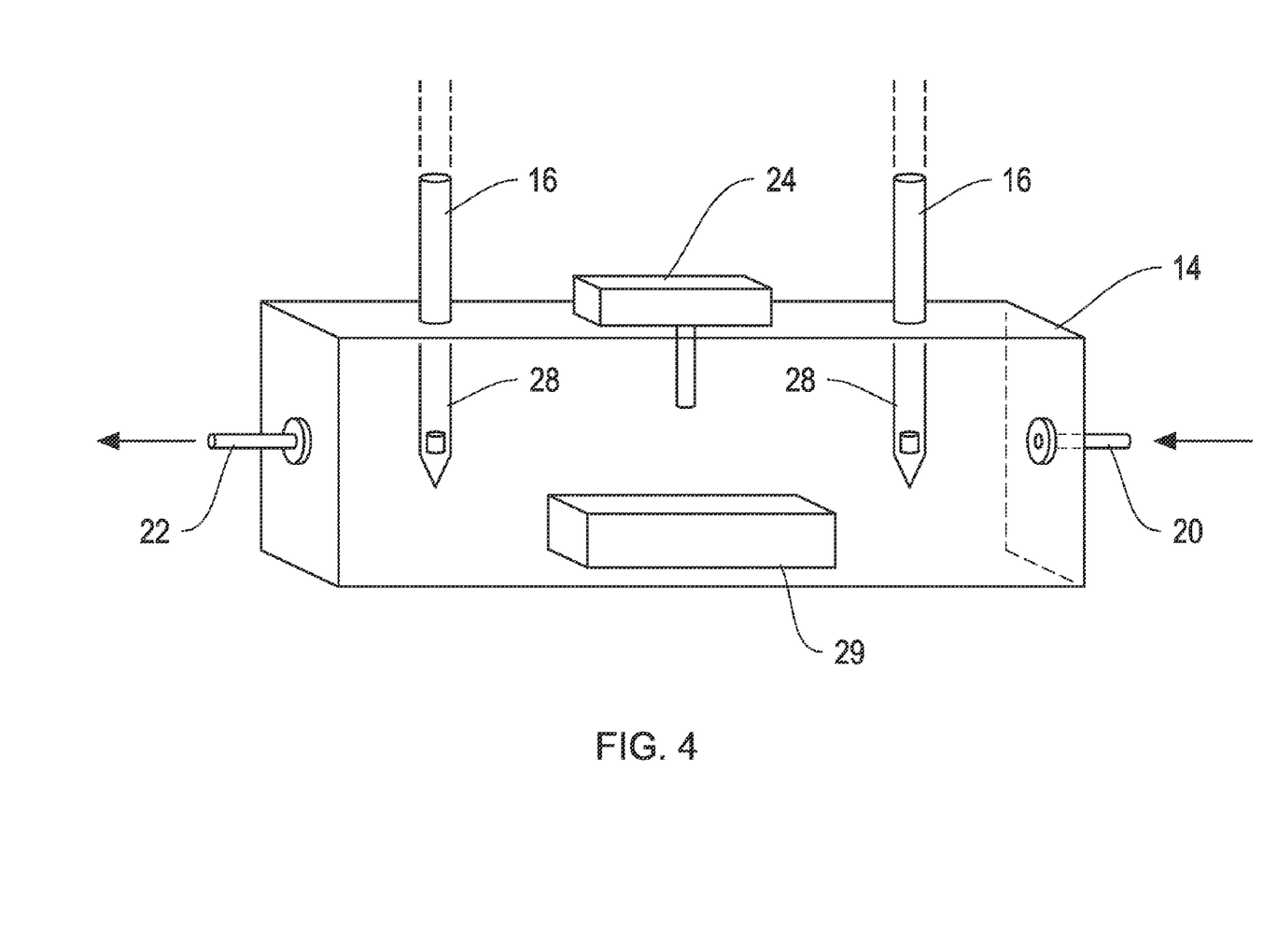
FIG. 4 depicts in more detail a mixing chamber of the type suitable for use in the seepage meter shown in FIG. 3B.

In FIG. 4, the sensors 16 are shown as being disposed within the mixing chamber 14. In particular, FIG. 4 depicts the mixing chamber 14, the stainless steel probes 16, a dye injector 24, an inlet/outlet port 20, an inlet/outlet port 22, and sensor ports 28 each of which are located at the distal end of the sensors 16. Also depicted in FIG. 4 is a mixing pump 29. The mixing pump 29 is disposed within the mixing chamber 14 and mixes the fluid within the chamber 14. Typically, the mixing pump 29 will mix the fluid in the chamber to keep the injected dye evenly mixed throughout the chamber 14. The mixing pump 29 may be a conventional electrical circulation pump of the type commonly used for circulating fluid in a tank or chamber.

As shown in FIG. 4 the absorbance meter 12 can have two sensors 16, although in other embodiments a single sensor may be used. The sensors 16 may be disposed at either end of the mixing chamber 14. The port 20 can be coupled with a source of groundwater discharge thereby allowing groundwater to flow into the interior of the mixing chamber 14. The port 22 can allow for the groundwater within the mixing chamber 14 to pass out of the chamber 14. The dye injector 24 can inject a water soluble dye into the interior of the mixing chamber of 14 thereby allowing the water soluble dye to mix with and color the groundwater flowing through the interior of the mixing chamber 14. The pump 29 may optionally be coupled at a point that is external to the mixing chamber 14, or located at some other position, and it will be understood that any suitable location for the pump 29 may be used as long as the pump is capable of evenly mixing the soluble dye with the fluid in the chamber 14. The pump may mix the dye in the chamber 14 by drawing water from the chamber 14 in one port and pumping it back into the chamber 14 through a second port. The pump 29 will mix the dye so that the dye is substantially evenly distributed throughout the fluid in the sample. This is understood to establish a uniform absorbance characteristic for the volume of fluid in the chamber 14. The pump 29 may optionally be operating continually to keep the dye evenly distributed throughout the chamber. This way changes in the absorbance characteristic may be modeled as representative of dilution of the dyed initial volume of fluid in the chamber by incoming volumes of non-dyed fluid entering the chamber through either of the ports 20 or 22 depending upon the flow of the groundwater. Additionally, the pump 29 may include a mechanism for flushing volumes of fluid from the mixing chamber 14, to eliminate or substantially eliminate the presence of dye or other injected substance within the mixing chamber 14.

The mixing chamber 14 is typically a plastic, such as plexiglass, chamber, that is sealed against the environment and that is optionally sufficiently transparent to allow a user to observe that dye is passing into the chamber 14 and mixing with the groundwater therein. In many cases it will be noted that the seepage meter may be placed at a location that is proximate the upland shore and in water depths that are sufficiently shallow to allow an above sea observer to visually monitor whether a colored dye or other material is present within the mixing chamber 14. The chamber 14 may be of any suitable size, volume and geometry and in one embodiment has an internal volume of about 50 mL to 1000 mL and more typically between 100 mL and 500 mL, however any suitable size may be used and the size selected will typically depend upon the application. One of the fiber optic sensors will extend outside of the chamber at location 22 so it may measure the background absorbance of the groundwater coming into the box. The second fiber optic sensor 16 may extend into the mixing chamber 14. Optionally, two or more sensors 16 may be placed in the chamber 14 or external to the chamber. The background absorbance may be used as a baseline value to help monitor the change in absorbance of groundwater contained in the mixing chamber 14.

Figure 5:
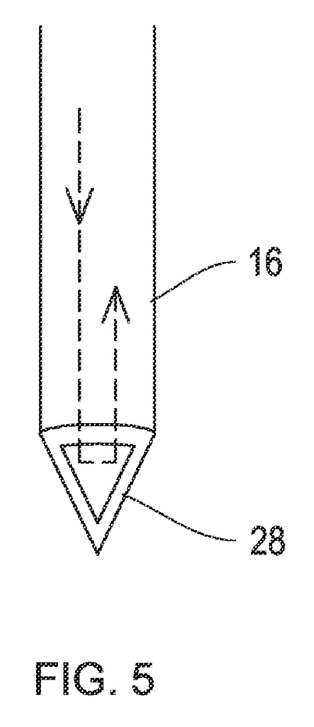
FIG. 5 depicts in more detail a reflective absorbance meter of the type suitable for use with the mixing chamber depicted in FIG. 4.

FIG. 5 illustrates that the seepage meter disposes an optical absorbance meter within the interior of the mixing chamber 14 so that measurements of the absorbance are made of fluid that is currently in the mixing chamber 14. This reduces the need for pumps that will withdraw the fluid from the chamber 14 to be analyzed in a separate analytical device. By eliminating this pump, the device may be made smaller and will use less power. The reduction in power usage is important as the seepage meter is often placed at a remote location and therefore requires stand alone operation off of a self-contained power supply such as a battery. In certain embodiments, the seepage meter may include a self-contained power generation system. This power generation system may be capable of generating power from a stored energy or fuel source, or may collect energy from the ambient environment. For example, the power generation system may comprise solar panels, wind turbines, tidal power generators, or any such power collection devices.

FIG. 5 shows in more detail one embodiment of the absorbance meter sensor probe 16. In particular, FIG. 5 shows that the fiber optic absorbance meter sensor probe 16 includes an open port 28. The open port 28 is open to the flow of groundwater and allows the groundwater or other fluid in the chamber to pass through the port 28. As shown in FIG. 5 a source of light, typically a light emitting diode of known wavelength or being switchable among multiple known wavelengths, directs a beam of light downward toward the port 28.

In the embodiment shown in FIG. 5 the port 28 includes two mirrored surfaces that are oriented at a 90 degree angle with respect to each other. The light passing through the sensor 16 in a downward direction reflects off the first mirror and is directed to the second mirror. Light from the second mirror is reflected upwardly back into the body of the sensor probe 16, and typically into an optical fiber. In this way a light path is established through the port 28. Accordingly, the amount of light that passes through the port 28 depends, at least in part, on the absorbance of any material that is passing through the port 28. The dyed groundwater will have an initial absorbance characteristic that is in part representative of the concentration of dye within the mixing chamber 14. The water soluble dye may be selected to be particularly interfered with and absorbed by the wave length of light being reflected between the two mirrors within the port 28. It may also be selected to provide a characteristic absorbance to the dyed groundwater that is different from the characteristic absorbance of groundwater or other typical environmental moieties that naturally occur or may be known to likely occur within the area where the meter is placed. In one embodiment, the light source generates light at a wavelength of about 590 nm and the dye injected into the mixing chamber is selected to be absorbed at or about that wavelength. In one particular embodiment, the light source and absorbance meter were of the type manufactured and sold by Ocean Optics, Inc. of Dunedin, Fla. In any case, the relative concentration of dye within the mixing chamber 14 may be monitored by measuring the amount of light that is absorbed while ground water passes through port 28. A series of time sequenced measurements will establish the rate at which the dye is being diluted by the passage of groundwater through the mixing chamber of 14. Over time the groundwater will carry away the injected dye and sensor 16 will no longer measure a changing absorbance characteristic of the material within the port 28.

FIG. 4 also illustrates the dye injector 24. As shown, the dye injector may be a simple injector that is mechanically coupled to the exterior of the mixing chamber 14 and that has an injection needle that extends into the interior of the mixing chamber 14. The dye injector may include an internal reservoir of concentrated dye and may, in one practice, inject about 1 mL of concentrated dye into the 500 mL chamber 14. The dye injector may be a solenoid operated pump of the type that is commercially available and may optionally include a coupling to a remote reservoir of dye material that can be drawn into the injector 24 and delivered into the chamber 14. The dye injector 24 may also include a timer that optionally runs under the control of a microprocessor or a microcontroller. The timer may generate a periodic timing signal that acts as a trigger for the solenoid pump to inject dye into the mixing chamber 14. For example, the dye injector 24 may connect to a microcontroller, such as a PIC microcontroller, that generates a timing signal having a period of for example 30 minutes. At thirty minute intervals the dye injector 24 can deliver a 5 mL dose of water-soluble dye into the mixing chamber 14. The pump 29 may be in continuous operation and will mix the dye with the fluid in the chamber 14. Over the next thirty minutes, before the next injection of dye, the absorbance meter may take a plurality of measurements of the absorbance characteristic of the fluid in the chamber 14. It is understood that groundwater seeping into or out of the section of ground being monitored will result in the dilution of the dyed fluid in the mixing chamber 14. This will decrease the absorbance characteristic of the fluid in the chamber 14 and the rate of dilution will be representative of the rate of flow of fluid into the mixing chamber 14.

In certain optional embodiments, the processor or controller may be programmed to change the timing of the dye injections based on the rate at which the dye is being diluted from the mixing chamber. Thus, if measurements of the rate at which dye is being flushed from the mixing chamber indicates that the mixing chamber 14 is devoid of dye after ten minutes, the controller can reduce the length of the period for injecting dye to, for example, a period of once every fifteen minutes. Alternatively, if the rate of dye being flushed from the system is very slow, the period may be extended. The controller will record the delivery time of the dye injections and record the measured absorbance levels and determine the rate of seepage. A real-time clock may be added so that the seepage rate data is correlated to the time of day, and thus to specific times and tidal conditions. In certain embodiments, the processor or controller may be programmed or configured to allow the seepage meter to operate in an automated fashion, i.e. without outside intervention or control, for some time.

Figure 6:
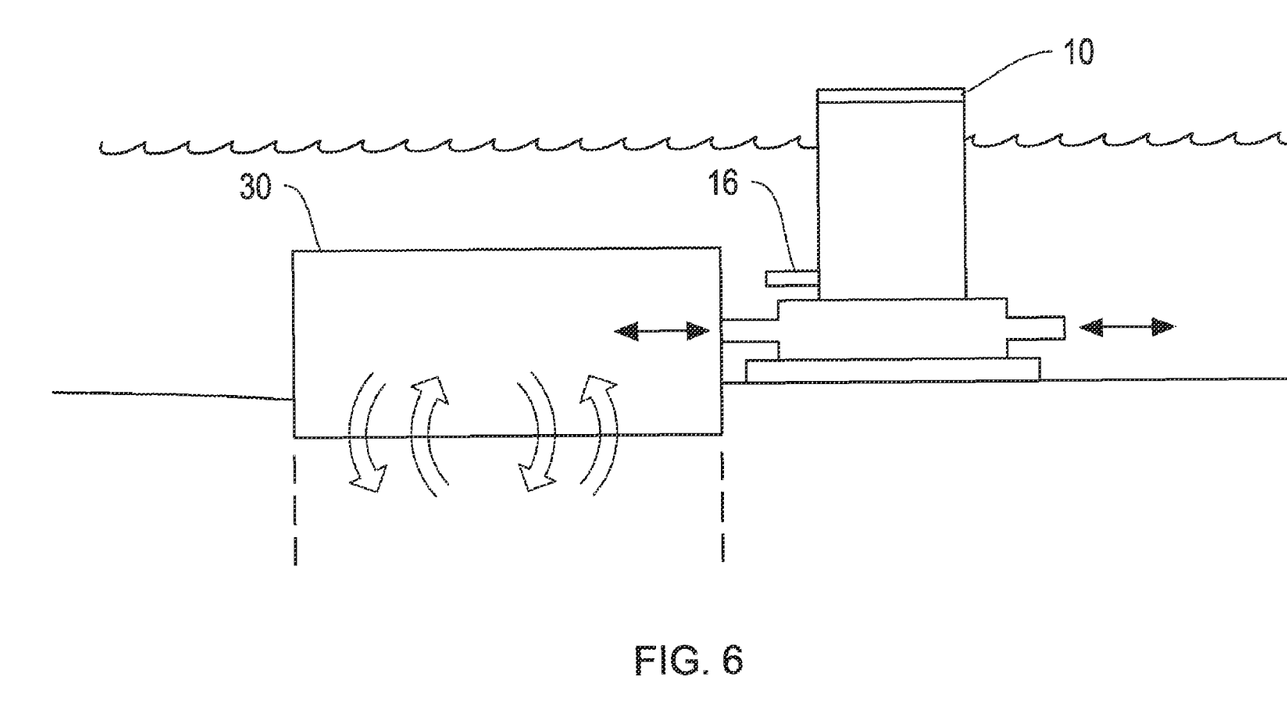
FIG. 6 depicts a seepage meter system and groundwater collection device according to an embodiment of the invention.

It will be noted that the device 10 may also be used to detect the direction of groundwater flow. For example, in one process the sensor probe 16 may be located between the mixing chamber 14 and the funnel, or at some other suitable location. The sensor 16 may be used to measure the absorbance characteristic of water pumped from the funnel, formed by a collar and collection chamber as shown in FIG. 6, and into the mixing chamber 14. If water pumped from the funnel appears to have dye contained therein then the indication is that surface water has been flowing into the sediment. If dye is absent from the water taken from the funnel, then the indication is that groundwater has been flowing out of the sediment. In other embodiments, other types of sensors, including mechanical flow sensors may be employed to determine the direction of groundwater flow. The collected flow rate information may be used to locate and operate intake pipes placed at the location of the best areas of SGD and the meters may be used to select which SGD sources, if any, the plant should use as a source of water for desalination.

FIG. 6 illustrates one embodiment of the seepage meter of FIG. 3B and a seepage housing 30 may sit over a portion of the sea floor and that captures the flow of groundwater and channels it through a port that connects to the mixing chamber 14. As shown in FIG. 6, the seepage meter 10 and the housing 30 may sit on the ocean floor and measure the flow of groundwater passing through the sediment that sits under the seepage housing 30. In this embodiment, the housing 30 includes a lower collar that sits against the ocean floor and seals a collection chamber inside the housing 30 against the ocean floor. In one embodiment, the housing 30 is a metal can that is open at the bottom. The side wall of the housing forms a collar that penetrates into the ocean floor a sufficient distance to form a seal around a section of the ocean floor. This seal keeps ocean water from leaking into the interior of the housing 30 from the sides. The side wall also forms a collection chamber that holds fluid that may be passing into the mixing chamber 14. In the depicted embodiment the housing penetrates about two or three inches (about 4 or 5 centimeters) into the ocean floor and the weight of the metal housing 30 is sufficiently large to keep the side wall of the housing 30 sealed against the ocean floor. Optionally, the housing may be sealed against the floor through other means, such as by using stakes that fix the housing 30 in place and sealed against the ocean floor. However, those of skill in the art will know other techniques for sealing the collar of the housing 30 against the ocean floor and any suitable technique may be employed.

In the embodiment depicted in FIG. 6, the collection chamber of the housing 30 is fluidly coupled to the mixing chamber 14 so that fluid passing through the section of ground surrounded by the collar and under the housing 30 passes through the depicted port and into the mixing chamber 14. In alternative embodiments, the mixing chamber may be at least partially open at the bottom and the mixing chamber 14 itself may seal against the ocean floor.

Figure 7:
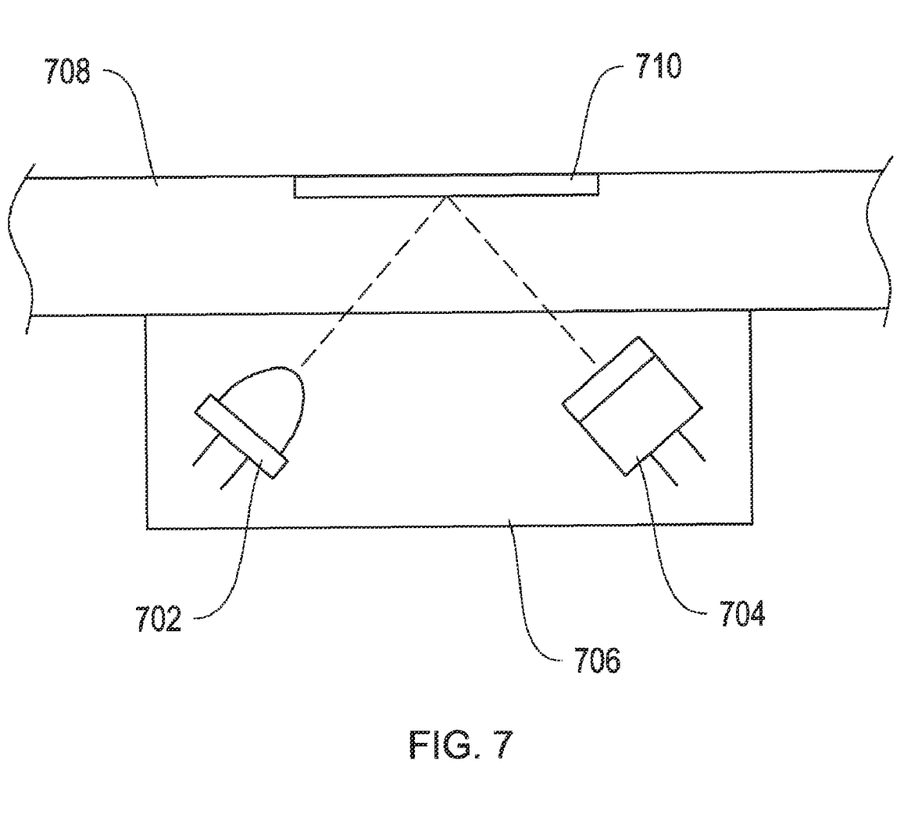
FIG. 7 depicts a light source and a light receiver passing a beam of light through fluid in the mixing chamber of FIG. 4, according to an embodiment of the invention.

FIG. 7 depicts an alternative embodiment of a sensor probe. In the depicted embodiment an LED 702 is mounted to a circuit board and a photodiode receiver 704 is mounted to the same board and is spaced away from the LED 702 to form a sensor 706. A fluid carrying channel 708 is placed in the light path between the LED 702 and the photodiode 704. The sensor 706 is sealed in a water tight package and may be placed into the mixing chamber 14. As described above with reference to FIG. 5, light from the LED passes through fluid in the channel 708 and may reflect off mirror 710. The photodiode 704 measures the intensity of light from the LED 702, which passes through the fluid and reflects off minor 708, and this provides a measure of the absorbance characteristic of the fluid in the channel 708. Multiple ones of such sensors may be placed in the mixing chamber at different respective locations.

The systems and methods described herein provide many advantages and benefits over the state of the art. These include, but are not limited to, providing systems that are less expensive that current configurations and may be made for about perhaps $6,000 to $8,000, as compared to the $25,000 cost of certain state of the art systems. These systems can have decreased power usage, allowing for longer deployment of the device than currently possible. The systems are less complex, having fewer moving parts, resulting in improved reliability. These systems may also achieve better time resolution, and data points are possible on time scales of seconds versus minutes. This can provide and the systems can achieve enhanced accuracy and the ability to detect and quantify contaminants contained within the flow of groundwater.

In other embodiments, other types of seepage meters may be employed and the type of meters used in the systems and methods described herein may vary according to the needs of the operation and conditions, such as the depth of the SGD being harvested. In some cases, even simple bag type seepage meters may be employed as least for some areas of the site being monitored.

Those skilled in the art will know or be able to ascertain using no more than routine experimentation, many equivalents to the embodiments and practices described herein. For example, the systems and embodiments described above have been shown as stand alone devices placed on the ocean floor. However, in other embodiments and configurations, the systems describe herein may be integrated into other devices and equipment on the ocean floor, including ocean floor observatories, sea floor mooring anchors and other devices. In certain embodiments and configurations, the seepage meters described herein may be provided with communication capabilities, either through a wired connection or a wireless connection, to each other or to one or more external sources. Further, it will be understood that the systems and methods described herein can be expanded to measure the flow of groundwater, as well as the flow of chemicals or other elements being carried in the groundwater, and further to measure other characteristics of a groundwater flow, such as the temperature or salinity of water seeping into the ocean. Additionally, the systems and methods described herein are largely discussed with reference to measuring seepage rates of groundwater into an ocean environment. However, the systems and methods described herein are not so limited in their applications and may be used to measure any type of fluid flow and the size and configuration of the devices may vary according to the application. Additionally, the systems and methods herein may be used to measure fluid flow into lakes, streams, and reservoirs as well as to measure fluid flow at underground/subsurface locations.

Accordingly, it will be understood that the invention is not to be limited to the embodiments disclosed herein, but is to be understood from the following claims, which are to be interpreted as broadly as allowed under the law.

The invention claimed is:

1. A method for detecting a source of submarine groundwater discharge suitable for processing by a desalination plant, comprising:
   providing at least one submersible seepage meter capable of measuring water salinity;
   disposing the at least one submersible seepage meter at at least one interface between a coastal aquifer and a body of saline water;
   measuring, with the at least one seepage meter, a flow of water through the at least one interface,
   measuring, with the at least one seepage meter, a flow direction of the flow of water through the at least one interface,
   measuring, with the at least one seepage meter, the salinity of the flow of water through the at least one interface, and
   detecting, with the at least one seepage meter, a location of the source of submarine groundwater discharge supplying the flow of water through the at least one interface, wherein the flow of water from the source of submarine groundwater discharge has at least one of a lower salinity than the body of saline water, and a flow direction towards the body of saline water.

2. The method of claim 1, wherein the at least one seepage meter is automated.

3. The method of claim 1, wherein the at least one seepage meter comprises a plurality of seepage meters disposed in a network for detecting the location of the source of submarine groundwater discharge supplying the flow of water through the at least one interface.

4. The method of claim 3, wherein the plurality of seepage meters includes a first seepage meter and a second seepage meter, the method comprising:
   measuring, with the first seepage meter, a first flow of water through the at least one interface, a flow direction of the first flow of water through the at least one interface, and the salinity of the first flow of water through the at least one interface, and
   measuring, with the second seepage meter, a second flow of water through the at least one interface, a flow direction of the second flow of water through the at least one interface, and the salinity of the second flow of water through the at least one interface, and
   detecting a location of the source of submarine groundwater discharge supplying the flow of water through the at least one interface based on at least one of the salinity and the flow direction of the first and second flows of water, wherein the first flow of water from the source of submarine groundwater discharge has at least one of a lower salinity than the second flow of water from the body of saline water, and a flow direction towards the body of saline water.

5. The method of claim 1, wherein the at least one interface is at the bottom of the body of saline water and the at least one seepage meter is submerged in the body of saline water and disposed on the bottom of the body of saline water.

6. The method of claim 1, wherein the at least one submersible seepage meter is a dye-dilution seepage meter, and includes
a mixing chamber having
a dye injector for making timed injections of a water soluble dye into the mixing chamber,
a pump for distributing the dye equally about the mixing chamber, and
an optical absorbance meter located within the mixing chamber and having a light source for passing a beam of light through the fluid flowing through the mixing chamber and a light receiver for measuring a characteristic representative of absorbance of a wavelength of light, and
a processor for processing the measured characteristic to determine a rate of flow for fluid passing through the at least one interface between the aquifer and the body of saline water.

7. The method of claim 6, wherein the at least one submersible seepage meter further includes a timer for making a series of timed measurements and dye injections for determining a rate of flow of water through the at least one interface between the aquifer and the body of saline water.

8. The method of claim 6, wherein the at least one submersible seepage meter further includes a background sensor for measuring a characteristic representative of absorbance of a wavelength of light of fluid in the mixing chamber and absent the injected dye.

9. The method of claim 1, wherein the at least one submersible seepage meter includes a sensor to measure a direction of fluid flow and wherein measuring the flow direction of the flow of water through the at least one interface comprises measuring the flow direction with the sensor.

10. The method of claim 1, wherein the at least one submersible seepage meter includes a chemical sensor for detecting at least one chemical element flowing through the at least one interface and for determining the rate of flow of the chemical through the at least one interface, and wherein measuring the salinity of the flow of water through the at least one interface comprises measuring the salinity with the chemical sensor.

11. A system for detecting a source of submarine groundwater discharge suitable for processing by a desalination plant, comprising:
at least one submersible seepage meter capable of measuring water salinity disposed at at least one interface between a coastal aquifer and a body of saline water and configured to:
measure a flow of water through the at least one interface,
measure a flow direction of the flow of water through the at least one interface,
measure the salinity of the flow of water through the at least one interface, and
detect a location of the source of submarine groundwater discharge supplying the flow of water through the at least one interface, wherein the flow of water from the source of submarine groundwater discharge has at least one of a lower salinity than the body of saline water, and a flow direction towards the body of saline water.

12. The system of claim 11, wherein the at least one seepage meter is automated.

13. The system of claim 11, wherein the at least one seepage meter comprises a plurality of seepage meters disposed in a network for detecting the location of the source of submarine groundwater discharge supplying the flow of water through the at least one interface.

14. The system of claim 11, wherein the at least one interface is at the bottom of the body of saline water and the at least one seepage meter is submerged in the body of saline water and disposed on the bottom of the body of saline water.

15. The system of claim 11, wherein the at least one submersible seepage meter is a dye-dilution seepage meter, and includes
a mixing chamber having
a dye injector for making timed injections of a water soluble dye into the mixing chamber,
a pump for distributing the dye equally about the mixing chamber, and
an optical absorbance meter located within the mixing chamber and having a light source for passing a beam of light through the fluid flowing through the mixing chamber and a light receiver for measuring a characteristic representative of absorbance of a wavelength of light, and
a processor for processing the measured characteristic to determine a rate of flow for fluid passing through the at least one interface between the aquifer and the body of saline water.

16. The system of claim 15, wherein the at least one submersible seepage meter further includes a background sensor for measuring a characteristic representative of absorbance of a wavelength of light of fluid in the mixing chamber and absent the injected dye.

17. The system of claim 11, wherein the at least one submersible seepage meter further includes a timer for making a series of timed measurements and dye injections for determining a rate of flow of water through the at least one interface between the aquifer and the body of saline water.

18. The system of claim 11, wherein the at least one submersible seepage meter includes a sensor to measure a direction of fluid flow and wherein measuring the flow direction of the flow of water through the at least one interface comprises measuring the flow direction with the sensor.

19. The system of claim 11, wherein the at least one submersible seepage meter includes a chemical sensor for detecting at least one chemical element flowing through the at least one interface and for determining the rate of flow of the chemical through the at least one interface, and wherein measuring the salinity of the flow of water through the at least one interface comprises measuring the salinity with the chemical sensor.

20. The system of claim 11, wherein the at least one submersible seepage meter includes a watertight housing.

* * * * *

UNITED STATES PATENT AND TRADEMARK OFFICE
CERTIFICATE OF CORRECTION

| | | |
|---|---|---|
| PATENT NO. | : 7,997,148 B2 | Page 1 of 1 |
| APPLICATION NO. | : 12/403287 | |
| DATED | : August 16, 2011 | |
| INVENTOR(S) | : Matthew Charette | |

It is certified that error appears in the above-identified patent and that said Letters Patent is hereby corrected as shown below:

In the specification

In Column 1, line 12 before "BACKGROUND OF THE INVENTION" the following should be inserted:

--STATEMENT OF RIGHTS TO INVENTIONS MADE UNDER FEDERALLY SPONSORED RESEARCH
This invention was made with Government support under Grant No. 0095384 awarded by the National Science Foundation. The Government has certain rights in this invention.--

Signed and Sealed this
Thirty-first Day of May, 2016

Michelle K. Lee
*Director of the United States Patent and Trademark Office*